United States Patent
Ogashiwa et al.

(10) Patent No.: US 8,026,491 B2
(45) Date of Patent: Sep. 27, 2011

(54) CHARGED PARTICLE BEAM APPARATUS AND METHOD FOR CHARGED PARTICLE BEAM ADJUSTMENT

(75) Inventors: Takeshi Ogashiwa, Hitachinaka (JP); Mitsugu Sato, Hitachinaka (JP); Atsushi Takane, Mito (JP); Toshihide Agemura, Hitachinaka (JP); Yuusuke Narita, Hitachinaka (JP); Takeharu Shichiji, Hitachinaka (JP); Shinichi Tomita, Hitachinaka (JP); Sukehiro Ito, Hitachinaka (JP); Junichi Katane, Naka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 383 days.

(21) Appl. No.: 11/715,506

(22) Filed: Mar. 8, 2007

(65) Prior Publication Data
US 2007/0284542 A1 Dec. 13, 2007

(30) Foreign Application Priority Data

Mar. 8, 2006 (JP) ................................. 2006-061980
Aug. 31, 2006 (JP) ................................. 2006-235871

(51) Int. Cl.
*G01N 21/00* (2006.01)

(52) U.S. Cl. .................. 250/396 R; 250/306; 250/307; 250/311; 250/491.1; 250/492.2

(58) Field of Classification Search ............... 250/491.1, 250/306, 307, 310, 311, 492.2, 492.3, 396 R, 250/397, 398, 399, 396 ML
See application file for complete search history.

(56) References Cited

U.S. PATENT DOCUMENTS

| | | | | |
|---|---|---|---|---|
| 4,524,277 A | * | 6/1985 | Shimura et al. | 250/397 |
| 5,180,919 A | * | 1/1993 | Oae et al. | 250/492.2 |
| 5,627,373 A | * | 5/1997 | Keese | 250/310 |
| 5,670,782 A | * | 9/1997 | Sato | 250/310 |

(Continued)

FOREIGN PATENT DOCUMENTS

JP 05-266840 10/1993

(Continued)

OTHER PUBLICATIONS

Japanese Office Action issued in Japanese Patent Application No. 2007-056534, mailed Dec. 14, 2010.

*Primary Examiner* — Robert Kim
*Assistant Examiner* — Michael Logie
(74) *Attorney, Agent, or Firm* — McDermott Will & Emery LLP

(57) ABSTRACT

A charged particle beam apparatus facilitating adjusting a beam center axis of a charged particle beam in a case where optical conditions are modified or in a case where the beam center axis of the charged particle beam is moved due to state variation of the apparatus. When the beam center axis of a primary charged particle beam is adjusted with a deflector (aligner), a first processing step for measuring the sensitivity of the aligner and a second processing step for detecting the deviation between the center of the primary charged particle beam and the center of the objective aperture are provided. The charged particle beam apparatus determines the aligner set values, using the aligner sensitivity measured in the first processing step and the amount of deviation detected in the second processing step, such that the primary charged particle beam passes through the center of the objective aperture and controls the aligner using the aligner set values.

5 Claims, 12 Drawing Sheets

U.S. PATENT DOCUMENTS

| | | | |
|---|---|---|---|
| 6,437,330 B1 * | 8/2002 | Sugiyama | 250/309 |
| 6,608,313 B2 * | 8/2003 | Simizu | 250/397 |
| 6,787,772 B2 * | 9/2004 | Ose et al. | 850/9 |
| 6,838,667 B2 * | 1/2005 | Tsuneta et al. | 850/10 |
| 6,864,483 B2 | 3/2005 | Olin | |
| 6,864,493 B2 * | 3/2005 | Sato et al. | 250/491.1 |
| 7,022,989 B2 * | 4/2006 | Inada et al. | 250/311 |
| 7,075,078 B2 * | 7/2006 | Ose et al. | 250/311 |
| 7,186,975 B2 * | 3/2007 | Ishitani et al. | 250/310 |
| 7,355,174 B2 | 4/2008 | Sato et al. | |
| 7,432,515 B2 * | 10/2008 | Nishimura | 250/492.23 |
| 2001/0010362 A1 * | 8/2001 | Simizu | 250/396 R |
| 2003/0127595 A1 * | 7/2003 | Nakamura et al. | 250/311 |
| 2003/0141451 A1 * | 7/2003 | Sato et al. | 250/310 |
| 2004/0222376 A1 * | 11/2004 | Sasaki et al. | 250/310 |
| 2005/0012050 A1 * | 1/2005 | Shemesh | 250/491.1 |
| 2005/0253083 A1 * | 11/2005 | Sato et al. | 250/398 |
| 2005/0274908 A1 * | 12/2005 | Tsai | 250/491.1 |
| 2006/0255269 A1 * | 11/2006 | Kawasaki et al. | 250/310 |
| 2007/0029478 A1 * | 2/2007 | Sato et al. | 250/310 |

FOREIGN PATENT DOCUMENTS

| | | |
|---|---|---|
| JP | 09069350 A * | 3/1997 |
| JP | 2000-133183 | 5/2000 |
| JP | 2002-352758 A | 12/2002 |
| JP | 2003-022771 | 1/2003 |
| JP | 2005-310699 A | 11/2005 |
| JP | 2006-012664 | 1/2006 |

* cited by examiner

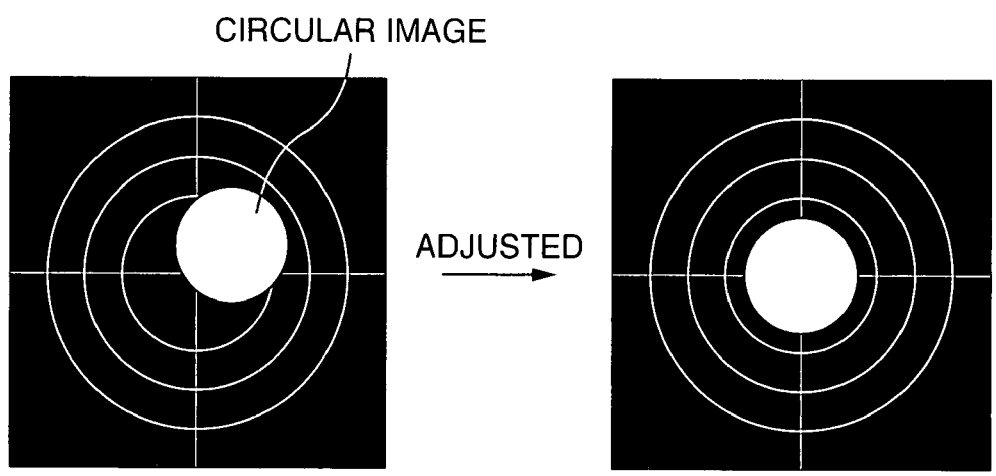

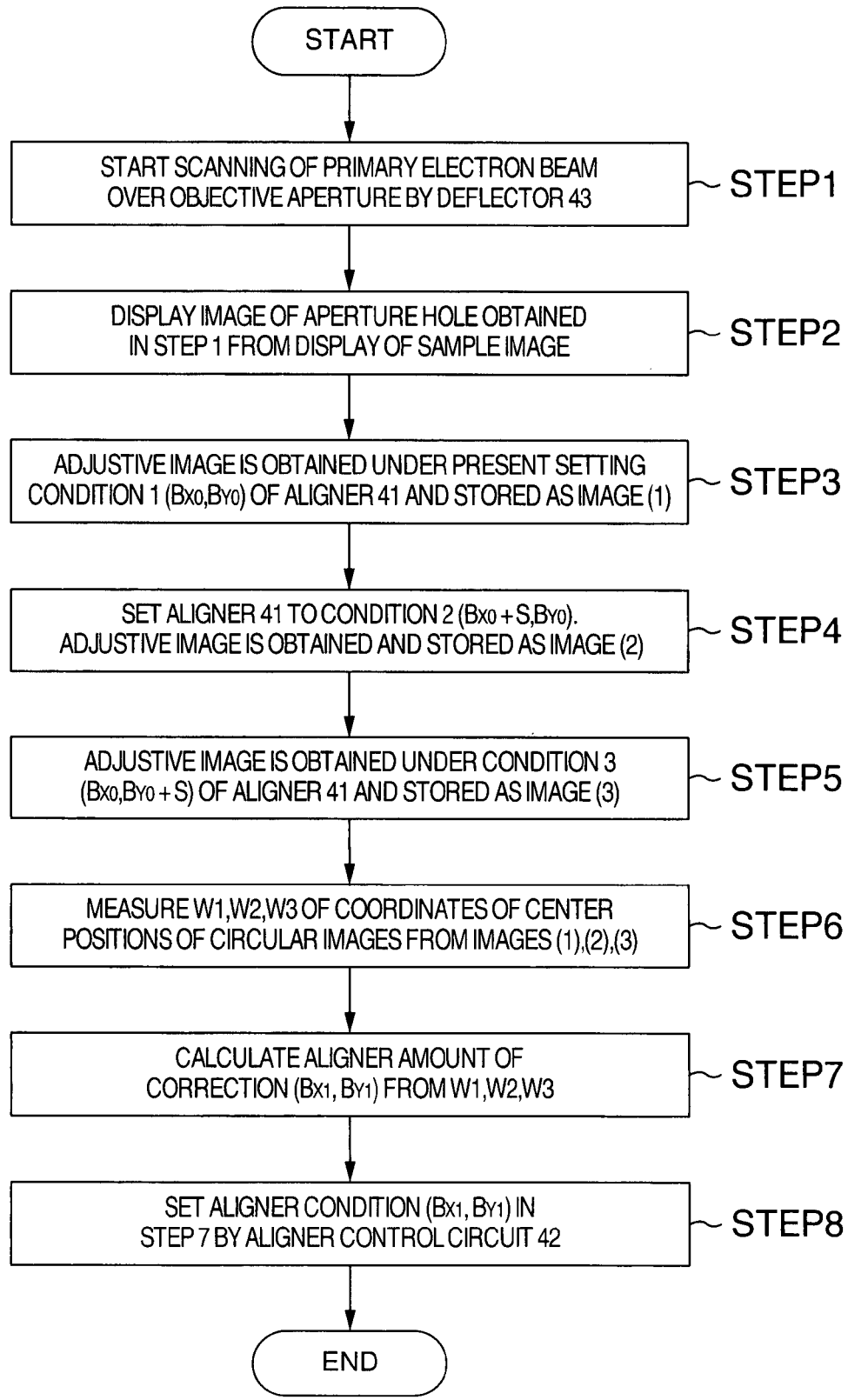

| REGION | DETECTION CONDITION | VARIATION OF ALIGNER |
|---|---|---|
| ① | Xmin ≦ -280 & Ymax ≧ +210 | +S IN X-DIRECTION AND -S IN Y-DIRECTION |
| ② | Xmin ≦ -280 | +S IN X-DIRECTION |
| ③ | Xmin ≦ -280 & Ymax ≦ -210 | +S IN X-DIRECTION AND +S IN Y-DIRECTION |
| ④ | Ymin ≦ -210 | +S IN Y-DIRECTION |
| ⑤ | Xmax ≧ +280 & Ymin ≦ -210 | -S IN X-DIRECTION AND +S IN Y-DIRECTION |
| ⑥ | Xmax ≧ +280 | -S IN X-DIRECTION |
| ⑦ | Xmax ≧ +280 & Ymax ≧ +210 | -S IN X-DIRECTION AND -S IN Y-DIRECTION |
| ⑧ | Ymax ≧ +210 | -S IN Y-DIRECTION |

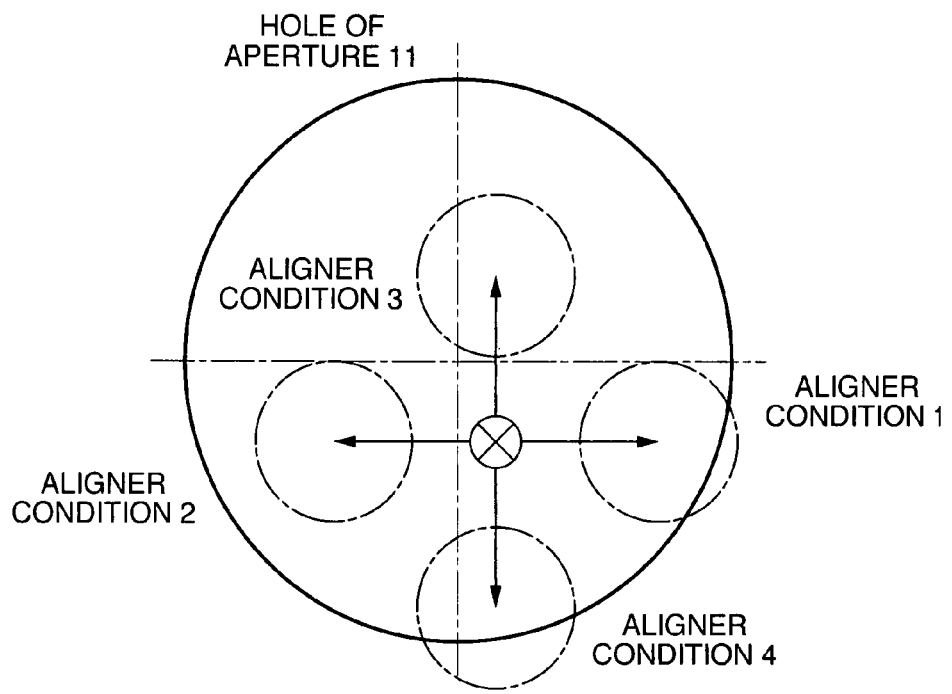

CHARGED PARTICLE BEAM APPARATUS AND METHOD FOR CHARGED PARTICLE BEAM ADJUSTMENT

BACKGROUND OF THE INVENTION

The present invention relates to a charged particle beam apparatus and, more particularly, to a charged particle beam apparatus in which a primary charged particle beam is allowed to easily pass through the center either of an objective aperture or of an aperture present within the orbit in which the charged particle beam passes, whereby the apparatus is adapted to obtain a high-brightness image stably.

In a charged particle beam apparatus typified by a scanning electron microscope, a sharply focused primary charged particle beam is scanned over a sample to obtain information (e.g., an image of the sample) from the sample. The microscope column of such a charged particle beam apparatus has an objective aperture for appropriately limiting the current hitting the sample (probe current). If there is a deviation between the center of the objective aperture and the center of the primary charged particle beam, the amount of the probe current of the primary charged particle beam limited by the objective aperture increases, thus decreasing the brightness of the sample image. In this case, appropriate control of the probe current cannot be achieved. It follows that a sample image of desired brightness cannot be obtained. Therefore, accurate adjustment is necessary to obtain a sample image of normal brightness by causing the primary charged particle beam to pass through the center of the objective aperture at all times. This adjustment is hereinafter referred to as the beam center axis adjustment.

Usually, in the beam center axis adjustment, a dedicated deflector is disposed over the objective lens. The primary charged particle beam is scanned over the objective aperture by the deflector, and an image of the objective aperture is obtained. An example of image of the objective aperture hole is shown in FIG. 2A. This image is created by a secondary signal produced by bombardment of the sample with the primary charged particle beam passed through the objective aperture. The center of the whole image (scanning center) is the center of the beam of the primary charged particle beam. The image of the white circular image is the image of the objective aperture hole. The center of the circle is the center of the objective aperture hole. In FIG. 2A, the center of the white circle deviates from the center of the image. Therefore, it can be seen that under this condition, the center of the primary charged particle beam does not pass through the center of the objective aperture hole during observation of the sample image.

Under the condition shown in FIG. 2A, to cause the primary charged particle beam to pass through the center of the objective aperture hole, the primary charged particle beam is moved into the center of the objective aperture hole, normally using a deflector (aligner) for adjustment of the beam center axis, the aligner being placed over the objective aperture. At this time, the image of the objective aperture is as shown in FIG. 2B. It is possible to bring the center of the whole image (scanning center) into coincidence with the center of the image of the objective aperture hole.

In the past, the aligner for adjustment of the beam center axis has been set manually by an operator while watching the image (image for adjustment) of the objective aperture hole. In one available method, means for storing aligner-setting conditions in relation to the optical conditions of the charged particle beam apparatus is mounted. During manipulation, the aligner-setting conditions are read out, and setting is done.

Furthermore, to automate the alignment, a technique for grasping the amount of axial deviation by image processing is disclosed in JP-A-2005-310699.

Furthermore, in a charged particle beam apparatus typified by a scanning electron microscope, a sharply focused charged particle beam is scanned over a sample, and desired information (e.g., an image of the sample) is obtained from the sample. In such a charged particle beam apparatus, if the optical axis deviates from the lens, lens aberration is produced, deteriorating the resolution of the sample image. Consequently, accurate axial adjustment is required in order to obtain a sample image at a high resolution. Therefore, in the prior-art axial adjustment, the excitation current of the objective lens or the like is varied periodically. The conditions under which the deflector (aligner) for axial adjustment operates are manually adjusted to minimize the motion produced at that time. A technique for automating such an adjustment is disclosed in JP-A-2002-352758 corresponding to U.S. Pat. No. 6,864,493.

This description reports a technique of a method of automatic axial adjustment. That is, under some deflection conditions of the alignment deflector, the objective lens conditions are varied to two conditions. The resulting image deviation is detected. The deviation between the images at two locations is applied to an equation. Optimum alignment conditions are found, and settings are made.

Furthermore, if there is a deviation from the center of the stigmator (astigmatic corrector) that performs astigmatic correction of the charged particle beam, the field of view is moved when astigmatism is adjusted. This makes it difficult to make the adjustment. Therefore, another aligner (deflector) for controlling the position of charged particles on the sample in an interlocking manner to the operation of the astigmatic corrector is provided. Motion of the image in response to variation of the set value of the stigmator (astigmatic corrector) is canceled out. Thus, the field of view is corrected such that the observed image does not move during adjustment of the astigmatism. A technique for automating this adjustment is also disclosed in JP-A-2002-352758 corresponding to U.S. Pat. No. 6,864,493.

There is a report of a technique for a method of automatic axial adjustment. In particular, the objective lens conditions are varied to two sets of conditions in some stigmator-deflecting conditions in the same way as the foregoing. The resulting deviation between images is detected. The deviation between the images at two locations is applied to an equation. Optimum alignment conditions are found, and settings are made.

SUMMARY OF THE INVENTION

To make a manual adjustment of the beam center axis by the method described above, sufficient techniques (manipulative experience) for manipulating the apparatus are necessary. Therefore, it takes a long time for a novice operator to complete the adjustment or the adjustment accuracy produces variations. Furthermore, in the method of performing settings by providing means for storing the aligner-setting conditions in relation to the optical conditions of the charged particle beam apparatus and reading out the aligner-setting conditions during manipulation, it is necessary that the aligner-setting conditions that vary depending on the optical conditions need to be stored for each set of optical conditions. Where a sample image is obtained after switching the optical conditions, it has been necessary to register and read out aligner-setting conditions whenever such a sample image is obtained. In addition, even if the apparatus is used under the same optical conditions, there is the problem that the adjustment accuracy is deteriorated by variation in the state of the apparatus provided that the registered aligner-setting conditions are used. For these reasons, there is the anxiety that the operator does not notice deviation of the beam center axis from the center of the objective aperture hole and that a sample image of normal brightness is not obtained.

Similar situations occur with the technique disclosed in JP-A-2005-310699. If a given control signal is applied to the aligner, desired deflection may not be achieved depending on the external environments or the state of the apparatus, Therefore, there is the problem that it is difficult to make an accurate alignment.

It is a first object of the present invention to provide a charged particle beam apparatus which permits one to adjust the beam center axis easily if the optical conditions are varied or if the beam center axis of the charged particle beam is moved due to variation in the state of the apparatus.

In the automated axial adjustment method described in JP-A-2002-352758 (corresponding to U.S. Pat. No. 6,864,493), in a case where an aperture for controlling the state either of the charged particle beam or of the sample chamber is present between the aligner and the sample, the charged particle beam is totally or partially blocked by the aperture depending on the conditions of the aligner. Consequently, the charged particle beam reaching the sample becomes different from the beam not yet passing through the aperture.

Where the above-described automated axial adjustment is made using the varied charged particle beam in this way, the beam does not fit the equation that derives a deviation of the sample image relative to a variation in the alignment condition. Consequently, the automated axial adjustment results in large error.

It is a second object of the present invention to provide method and apparatus which are used in a charged particle beam apparatus having an aperture under the aligner to implement the aforementioned automated method of axial adjustment more accurately.

The first object described above is achieved by a first aspect of the present invention. In this aspect, when the beam center axis of the charged particle beam is adjusted with a deflector (aligner), processing steps (1) and (2) are carried out. In the step (1), the sensitivity of the aligner is measured. In the step (2), the deviation between the center of the primary charged particle beam and the center of the objective aperture is detected. Aligner control means is provided which determines values set for the aligner, using the aligner sensitivity measured in the step (1) and the amount of deviation detected in the step (2), such that the primary charged particle beam passes through the center of the objective aperture. The control means controls the aligner using the values set for the aligner.

The aforementioned second object is achieved by one embodiment of the invention that is a charged particle beam apparatus having a source of charged particles, an alignment deflector for adjusting the axis of a charged particle beam released from the source of charged particles relative to an objective lens and/or a stigmator, and an image based on the charged particles released from a sample. The charged particle beam apparatus is equipped with a device for evaluating the brightness of the image when the alignment deflector is varied to at least two sets of deflecting conditions and calculating conditions under which the aligner deflector is adjusted, using the brighter image out of the at least two deflection conditions.

According to the first aspect of the present invention described so far, deflection is performed after finding the sensitivity of the alignment deflector and so accurate alignment can be accomplished without depending on the conditions of the apparatus.

According to the second embodiment of the present invention described so far, even if an aperture is present under the aligner, accurate axial adjustment is possible regardless of the optical conditions of the charged particle beam.

Other objects, features and advantages of the invention will become apparent from the following description of the embodiments of the invention taken in conjunction with the accompanying drawings.

BRIEF DESCRIPTION OF THE DRAWINGS

FIGS. 2A and 2B are examples of image of an objective aperture hole.

FIG. 3 is a flowchart for implementing an embodiment of the present invention.

FIG. 12 is a diagram illustrating the principle of production of vignetting of a charged particle beam due to an apertured plate.

FIG. 13 is schematic flow 2 of processing for correcting axial deviation relative to the objective lens.

DESCRIPTION OF THE EMBODIMENTS

Embodiment 1

Measurement of the sensitivity of an aligner performed in the processing step (1) and detection of the deviation between the center of the primary charged particle beam and the center of the objective aperture are described, the detection being performed in the processing step (2).

The aligner can align the primary charged particle beam normally in X-, and Y-directions (in two dimensions). The initial condition of the aligner is given by $(X_0, Y_0)$. The amount of correction of the aligner is given by $X_1, Y_1$. Where the center position $W_{ALB}$ of a circular image on the image used for adjustment of the beam center axis is represented by complex numbers, the relationship given by the following Eq. (1) is obtained.

$$W_{ALB} = C + D \cdot (X_1 + j \cdot \epsilon \cdot Y_1) \quad (1)$$

where C is a complex representation of the amount of deviation between the center of the image for adjustment of the beam center axis and the center of the circular image, D is a complex representation of the sensitivity of motion of the circular image corresponding to an alignment signal X in the X-direction, and $\epsilon$ is a complex representation of the relative sensitivity of the aligner in the Y-direction relative to the X-direction. The relative sensitivity indicates the sensitivity ratio and the orthogonal deviation of the aligner. The purpose of adjustment of the beam center axis corresponds to finding of the amount of correction $X_1$ and $Y_1$ of the aligner at which $W_{ALB}$ shown in Eq. (1) is reduced to 0. Therefore, the amount of correction $X_{opt}$, $Y_{opt}$ of the aligner for setting the left side of Eq. (1) to 0 has the relationship given by Eq. (2).

$$X_{opt} + j\epsilon \cdot Y_{opt} = -\frac{C}{D} \quad (2)$$

In this equation, $\epsilon$ and C/D are unknown numbers and so each component of the amount of correction of the aligner ($X_1$, $Y_1$) is varied by S, and the coordinates of the center position of the circular image on the image for adjustment of the beam center axis obtained at this time are measured by image processing. The relationship of the center position $W_{ALB}$ of the circular image relative to the amount of variation of the aligner is shown in Table 1. Various methods are available as the image processing technique for finding the center position of the circular image and are well known in the art.

TABLE 1

| amount of variation of aligner ($AL_1$) | | center position ($W_{AL1}$) of circular image on image for adjustment of beam center axis |
|---|---|---|
| $X_1$ | $Y_1$ | $W_{AL1} = C + D \cdot (X_1 + j \cdot \epsilon \cdot Y_1)$ |
| 0 | 0 | $W_1 = C$ |
| S | 0 | $W_2 = C + D \cdot S$ |
| 0 | S | $W_3 = C + j \cdot \epsilon \cdot D \cdot S$ |

Figure 1:
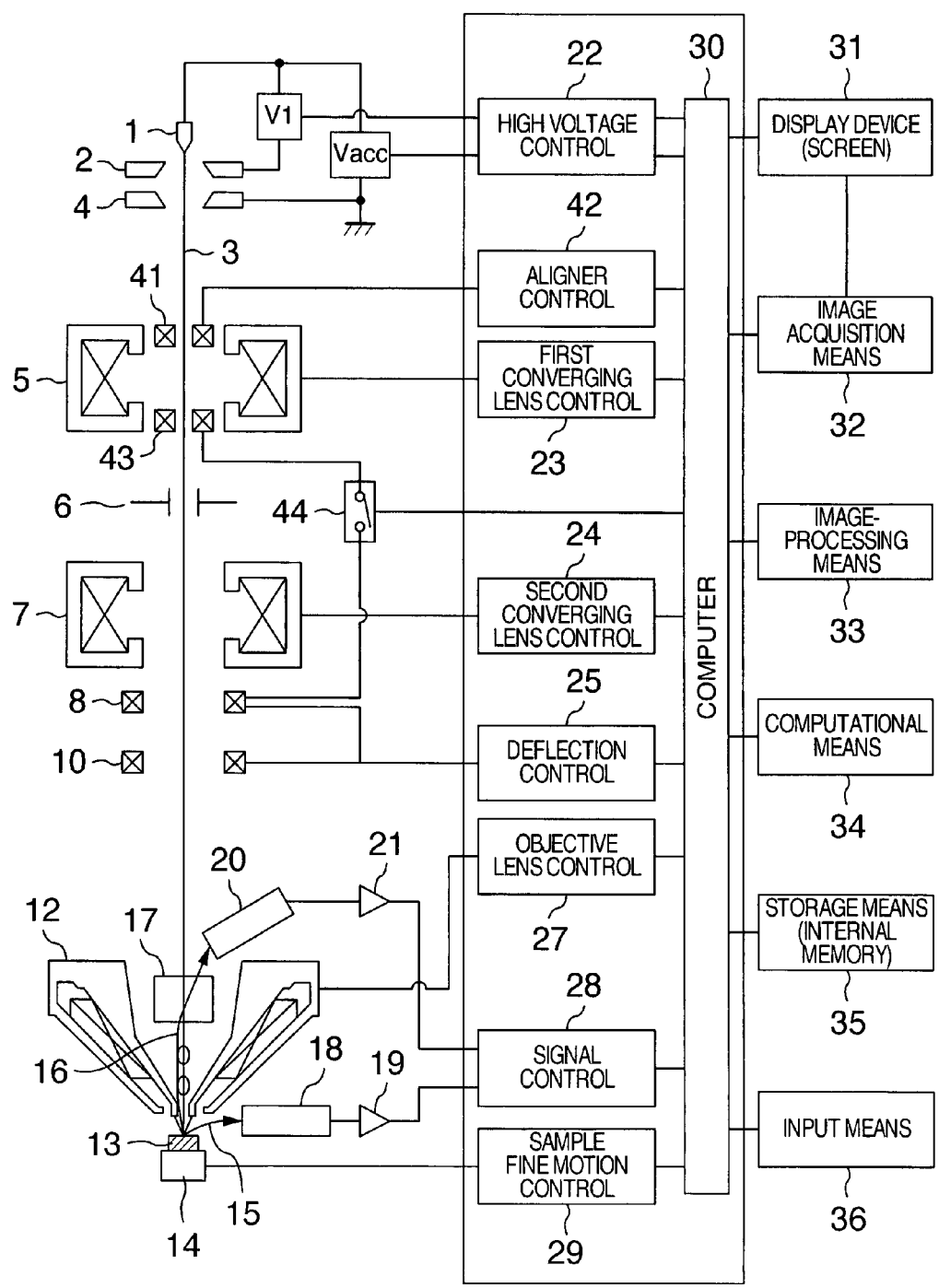
FIG. 1 is a schematic diagram of a scanning electron microscope.

Solving $\epsilon$ and C/D from the center position ($W_1$, $W_2$, $W_3$) of the circular image on the image for adjustment of the beam center axis shown in FIG. 1 gives rise to relationships given by Eqs. (3) and (4), respectively.

$$\varepsilon = -j \cdot \frac{W_3 - W_1}{W_2 - W_1} \quad (3)$$

$$\frac{C}{D} = \frac{W_1 \cdot S}{W_2 - W_1} \quad (4)$$

The amount of correction ($X_{opt}$, $Y_{opt}$) of the aligner can be found by substituting the results of Eqs. (3) and (4) into Eq. (2). $W_3-W_1$ is a first image deviation obtained when one of two deflectors is adjusted. $W_2-W_1$ is a second image deviation obtained when the other of the deflectors is adjusted. In the present embodiment, the sensitivity of the deflectors for alignment is detected based on the two image deviations.

An embodiment of the present invention is hereinafter described in detail with reference to the drawings. FIG. 1 is a schematic view of one embodiment of the present invention, and is one of charged particle beam apparatus. This is a scanning electron microscope equipped with a field emission gun. It is to be noted that the advantages of the invention are not limited by the equipped electron gun. A primary electron beam 3 released from a cathode 1 by a voltage V1 applied to the cathode 1 and a first anode 2 is accelerated to the voltage Vacc applied to a second cathode 4 and travels to a rear stage of electromagnetic lens system. The accelerating voltage Vacc and V1 are controlled by a high-voltage control circuit 22. The primary electron beam 3 is converged by a first converging lens 5, which in turn is controlled by a first converging lens control circuit 23.

With respect to the primary electron beam 3, the current hitting the sample is limited by an objective lens aperture 6 disposed closer to the cathode 1 (closer to the source of charged particles) than the objective lens 6. An aligner 41 for adjustment of the beam center axis, an aligner control circuit 42, and a deflector 43 for adjustment of the center axis of the beam to scan the beam over the objective lens aperture 6 are provided to make the center of the beam pass into the center of the hole of the objective lens aperture 6.

Furthermore, the primary electron beam 3 is again converged by a second converging lens 7, which in turn is controlled by a second converging lens control circuit 24. The beam 3 is sharply focused onto a sample 13 by the objective lens 12, which in turn is controlled by an objective lens control circuit 27. The beam is scanned over the sample 13 in two dimensions by an upper stage of deflection coil 8 and a lower stage of deflection coil 10 with which a deflection control circuit 26 is connected. When an image for adjustment of the beam center axis is obtained, the present scan signal is connected with the deflector 43 for adjustment of the beam center axis via a relay switch 44. The signal is synchronized with a scan signal for the deflection coil 9 and operated.

The sample 13 lies over a sample fine motion driver 14 that is controlled by a sample fine motion control circuit 29. Of signals produced from the point of the sample 13 irradiated with the primary electron beam, energetic reflected electrons 15 released at relatively shallow angles are detected by a detector 18 and amplified by an amplifier 19. Secondary electrons 16 having lower energies are wound up by the magnetic field produced by the objective lens 12. An orthogonal electromagnetic field (EXB) device 17 disposed over the objective lens permits the secondary electrons to be detected by a detector 20 without producing axial deviation of the primary electron beam 3. The signal is amplified by an amplifier 21.

The amplifiers 19 and 21 are controlled by a signal control circuit 28. The various control circuits 22-29 including the control circuit 28 are controlled by a computer 30 that controls the whole apparatus. The amplified signals of the secondary and reflected electrons are displayed as magnified images of the sample on the screen of a display device 31.

Image acquisition means 32 for deriving observational images displayed on the display device 31 as image information, image-processing means 33 for performing various kinds of image processing on the observational images, computational means 34 for calculating the sensitivity parameter of the aligner and performing various other calculations from the results of the image processing, an internal memory 35 for saving the observational images and the results of the calculations, and input means 36 for entering observational conditions are also connected with the computer 30.

Figure 4A:
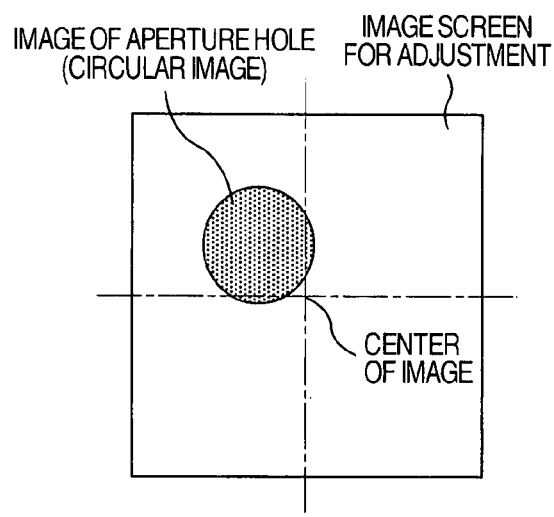
FIGS. 4A, 4B, 4C, and 4D are schematic views illustrating the manner of an adjustive image for adjustment of the beam center axis.
Figure 4B:
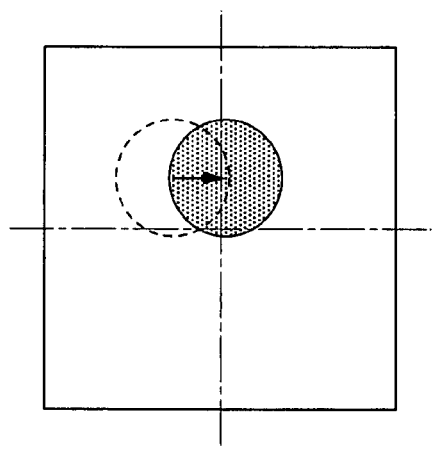
Figure 4C:
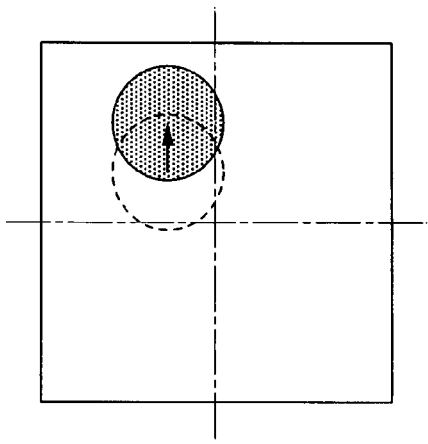
Figure 4D:
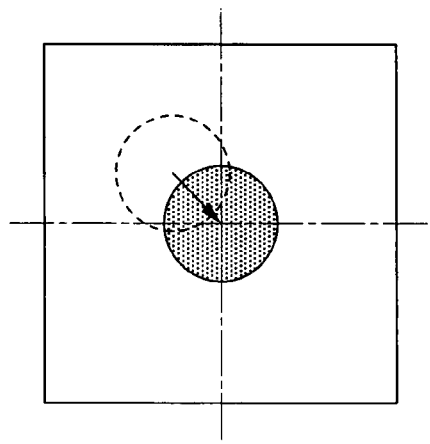

A method of adjusting the beam center axis using the present invention is next described in detail with reference to FIGS. 3 and 4A, B, C, and D. FIG. 3 illustrates the flow of processing for adjustment of the beam center axis in the present embodiment. A program for processing this is registered as a program in the internal memory 35 and processed under instructions from the computer 30. FIG. 4 schematically illustrates the manner of displayed images for adjustment of the beam center axis in the present embodiment:

In step 1, scanning of the primary electron beam 3 over the objective lens aperture 6 is started by the deflector 43 for adjustment of the beam center axis.

In step 2, an image (adjustive image) of the aperture hole obtained from step 1 is displayed from the sample image displayed on the display device 31.

In step 3, the adjustive image is obtained using the image acquisition means 32 under present set conditions (1) ($B_{X0}$, $B_{Y0}$) for the aligner 41 for adjustment of the beam center axis. The adjustive image is stored as image (1) in the internal memory 35. At this time, the displayed image assumes the state shown in FIG. 4(a).

Figure 8:
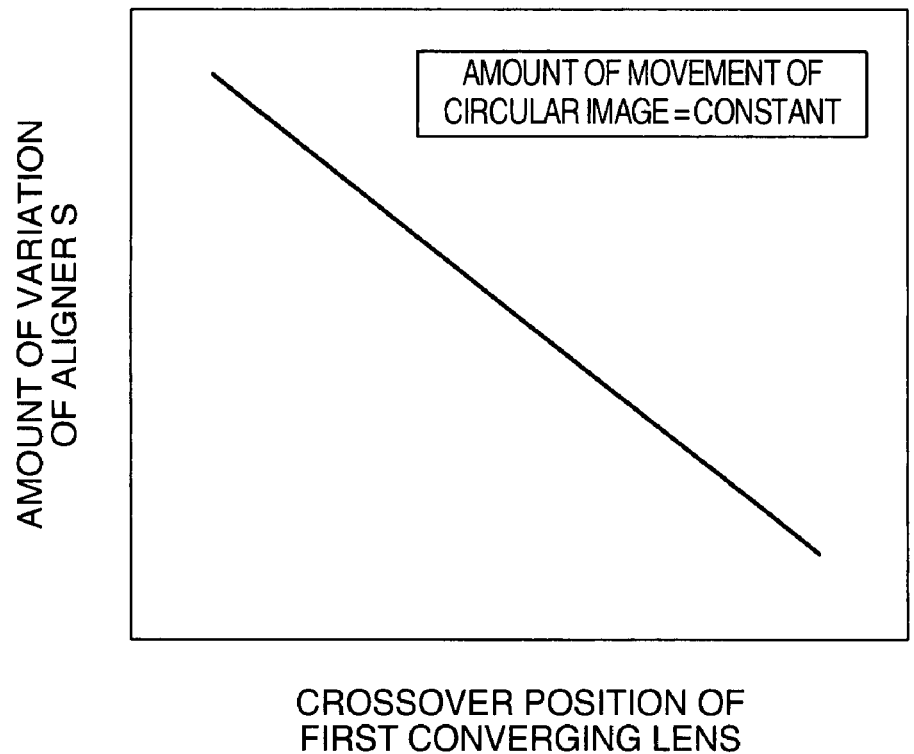
FIG. 8 is a relationship between the crossover position of a first converging lens and the amount of variation S of the aligner.

In step 4, the aligner 41 for adjustment of the beam center axis is set to condition (2) ($B_{x0}$+S, $B_{y0}$). An adjustive image is acquired in the same way as in step 3 and stored as image (2). At this time, the displayed image assumes the state shown in FIG. 4(b).

Where the aligner 41 for adjustment of the beam center axis is set to the condition (2) ($B_{X0}$+S, $B_{Y0}$), the amount of movement of the circular image within the adjustive image is preferably constant at all times, for the following reason. If the amount of movement is too large, there is the possibility that the circular image protrudes from the image region of the adjustive image. Conversely, if the amount of movement is too small, there is the possibility that the apparatus judges that the circular image has not been moved by image processing. Where the amount of movement of the circular image is kept constant at all times, a relationship as shown in FIG. 8 is present between a focal point (crossover position) of the primary electron beam 3 converged by the first converging lens 5 and the amount of variation of the aligner. Accordingly, variations of S relative to the crossover position of the first converging lens 5 are previously registered in the apparatus. When an amount of variation of S is given to the aligner, the amount of movement of the circular image within the adjustive image can be kept constant at all times if the presently set crossover position of the first converging lens 5 is read out.

In step 5, the aligner 41 for adjustment of the beam center axis is set to condition (3) ($B_{X0}$, $B_{Y0}$+S), an adjustive image is acquired in the same way as in step 3, and stored as image (3). At this time, the displayed image assumes the state shown in FIG. 4C.

In step 6, the coordinates $W_1$, $W_2$, and $W_3$ of the center position of the circular image on the image for adjustment of the beam center axis are measured from images (1), (2), and (3) by image processing. The measurement of the center position of the circular image can be carried out, for example, by a known image-processing technique registered in the image-processing means 33. Furthermore, this may be replaced by finding of the position of the center of gravity of the circular image. The coordinates of the center position of the circular image are stored in the internal memory 35.

In step 7, the amount of correction ($B_{X1}$, $B_{Y1}$) to the aligner is determined from the coordinates of the center position of the circular image found in step 6 by a computational procedure shown in the above calculational formulas (1)-(4).

In step 8, the amount of correction ($B_{X1}$, $B_{Y1}$) to the aligner determined in step 7 is set into the aligner 41 for adjustment of the beam center axis through the aligner control circuit 42. At this time, the displayed image assumes the state shown in FIG. 4D.

Because of the processing steps described so far, when the adjustment of the beam center axis is carried out, any steps for manual adjustment as in the prior art are eliminated. Hence, the adjustment can be automated. As a result, where the optical conditions are modified or the beam center axis of the charged particle beam has moved due to variation of the state of the apparatus, it is easy for a novice operator to adjust the beam center axis.

Before the present processing is performed, a step for calculating the width of scanning made by the deflector 43 for adjustment of the beam center axis over the objective aperture according to the focal point (crossover position) of the primary electron beam converged by the first converging lens 5 and setting the width may be provided. Consequently, an image (circular image) of the objective aperture hole is displayed in a size that is kept constant at all times on the adjustment screen. The accuracy at which the beam center axis is adjusted can be improved.

Furthermore, in order to detect the center position of the circular image at high accuracy by image processing, the circular image needs to have uniform and homogeneous brightness. However, the circular image may often contain image information about the structure of the sample and image information about the geometry of the objective lens. Accordingly, prior to execution of the present processing, a processing step for reducing the two-dimensional scanning width of the primary electron beam over the sample by the upper stage of deflection coil 8 and lower stage of deflection coil 10 may be performed. Moreover, a processing step for modifying the brightness or contrast of the circular image from the conditions used when the sample image is displayed and appropriately setting the brightness or contrast may be performed.

In addition, a processing step for modifying the state of the objective lens 12 in which the contour of the circular image is not affected to conditions in which the beam is not focused onto the sample through the objective lens control circuit 27 may be performed. Because of the steps described so far, neither information about the secondary electron image of the objective lens 12 nor information about the secondary electron image about characteristic structures of the sample contained in the sample 13 is contained in the image (circular image) of the objective aperture hole. A circular image having ever constant brightness and contrast can be displayed. Therefore, erroneous detection of the coordinates of the center position of the circular image by image processing can be reduced. Accurate adjustment of the beam center axis can be carried out.

Furthermore, in the present embodiment, a processing step A as described below can be added between the steps 2 and 3 of FIG. 3 to improve the accuracy of adjustment.

First, detection of the circular image under the initial condition of the aligner is described in detail.

Figure 5:
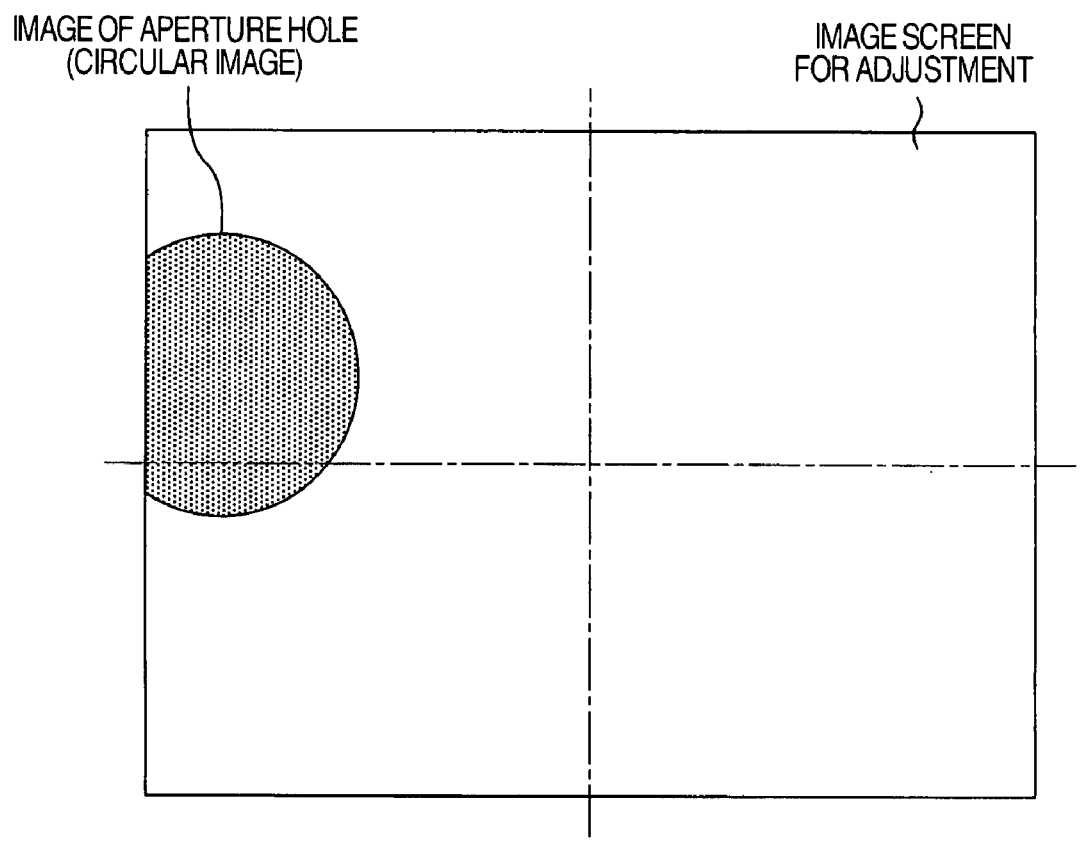
FIG. 5 is a schematic diagram showing the state in which a circular image within the adjustive image is shifted excessively toward an end.

Depending on the initial condition of the settings of the aligner, the circular image may be shifted excessively toward an end of the adjustive image as shown in FIG. 5, and parts of the circle may not be displayed. In this case, when the circular image is recognized by image processing and the center of the circle is found, there is the possibility that a position different from the actual center position of the circle may be misrecognized as the center of the circle. This may greatly deteriorate the accuracy at which the beam center axis is adjusted. Accordingly, in a case where the adjustive image is acquired using the image acquisition means 32 under the present set conditions (1) ($B_{X0}$, $B_{Y0}$) for the aligner 41 for adjustment of the beam center axis (i.e., the state of the above-described step 3), if a circular image is present outside the image region that is the adjustive image, the aligner is so controlled that the circular image moves toward the center of the adjustive image. This is described by referring to FIGS. 6 and 7.

Figures 6, 7:
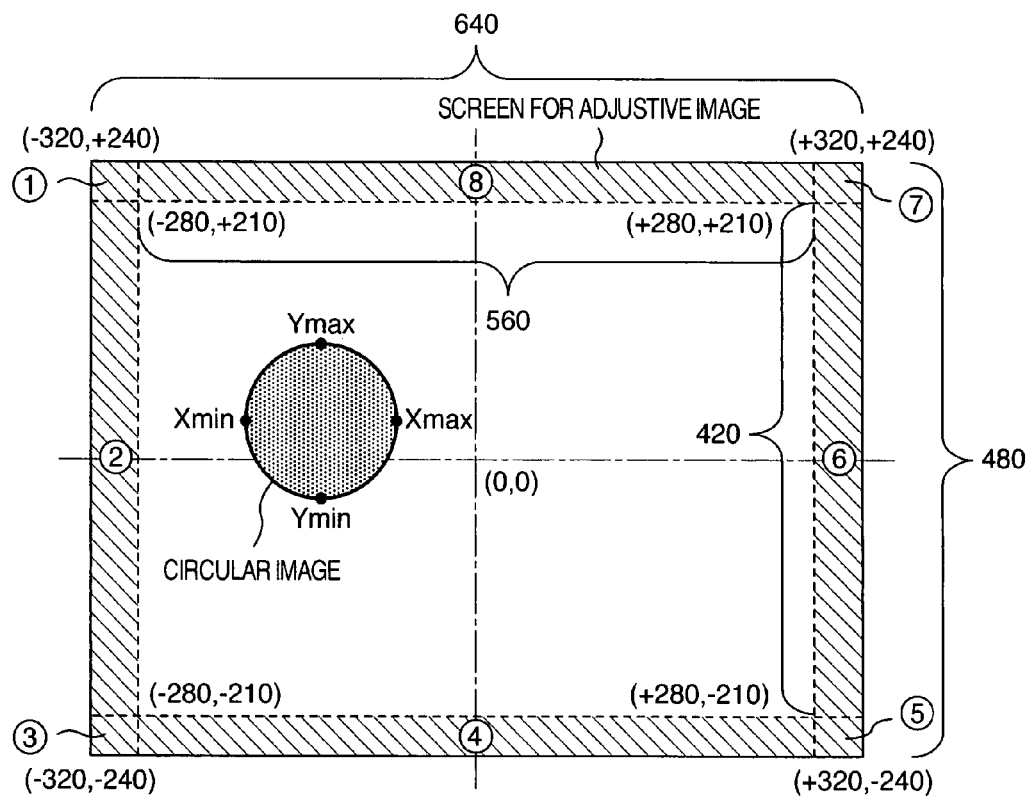
FIG. 6 is an explanatory view illustrating a method of judging whether the circular image is at an end of the adjustive image.
FIG. 7 is a table of a set of conditions under which a decision is made as to whether the circular image is at an end of the adjustive image.

In FIG. 6, the whole region of the adjustive image used for adjustment of the beam center axis is assumed to be composed of 640×480 pixels. At this time, it is assumed that the coordinates of the center of the image are given by (0, 0). The coordinates of the four corners of the image are as shown in FIG. 6. When a part of the circular image displayed within the adjustive image is present outside some image region (e.g., ⅞ of the whole adjustive image consisting of 560×420 pixels), the aligner is controlled such that the circular image is moved a given amount toward the center. For example, a variation of S occurs.

A decision is made as to whether the circular image is present in this region as illustrated in FIG. 6. Maximum value (Xmax) and minimum value (Xmin) of the circular image portion in the X-direction are found by image processing. Also, maximum value (Ymax) and minimum value (Ymin) of the circular image portion in the Y-direction are found by image processing. Then, a decision is made as to whether these values fit the conditions listed in the table of FIG. 7. For example, where Xmin=−300 and Ymax=+210 (the image protrudes from the adjustive image region in the Y-direction), (1) in the table of FIG. 7 applies. Therefore, the aligner is controlled such that the circular image varies by +S in the X-direction and varies by −S in the Y-direction.

The processing step A described so far eliminates the anxiety that the circular image is shifted excessively to an end within the adjustive image; otherwise, the whole circle would not be displayed. In consequence, the accuracy at which the beam center axis is adjusted can be improved.

Embodiment 2

An embodiment of the present invention is described below with reference to the drawings.

Figure 9:
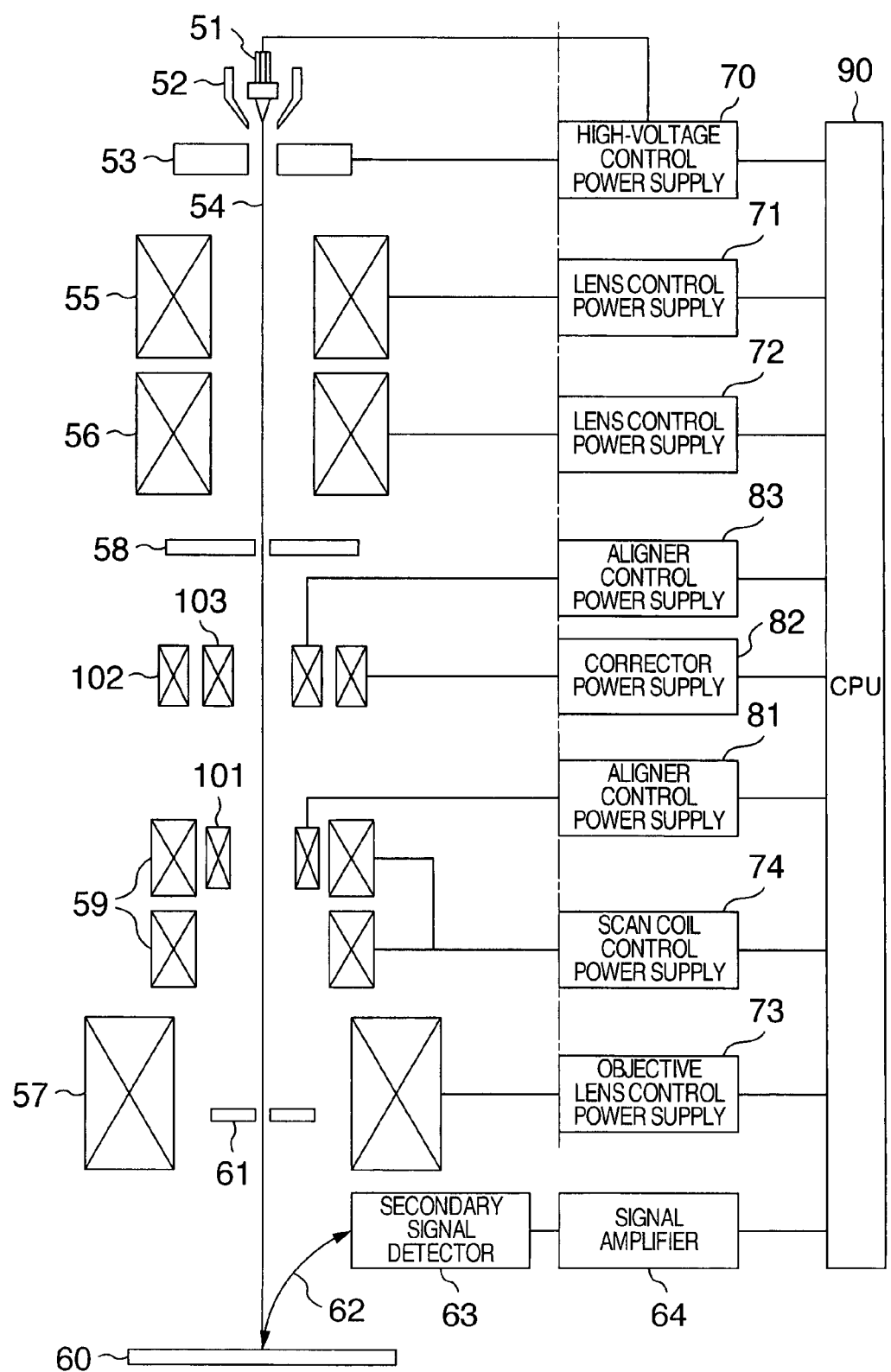
FIG. 9 is a schematic diagram of a scanning electron microscope that is one example of the present invention.

FIG. 9 is a schematic diagram of a scanning electron microscope that is one example of the present invention. Voltages are applied to a filament 51 and an anode 53 by a high-voltage control power supply 70 that is under control of a microprocessor (CPU) 90. A primary electron beam 54 is pulled out from the filament 51 with a given emission current. An accelerating voltage is applied between the filament 51 and the anode 53 by the high-voltage control power supply 70 that is under control of the CPU 90. The primary electron beam 54 released from the cathode 51 is accelerated and travels to the following stage of lenses. The primary electron beam 54 is converged by converging lens 55 and 56 that are under control of lens control power supplies 71 and 72. Unwanted regions of the primary electron beam are removed by an apertured plate 58 and then the beam passes through an apertured plate 61 in the neighborhood of the objective lens. The beam is focused as a quite small spot on a sample 60 by the objective lens 57 that is controlled by an objective lens control power supply 73. The objective lens 57 is so designed that it varies the focal conditions for the primary electron beam 54 by an electrical current supplied from the objective lens control power supply 73.

The primary electron beam 54 is scanned according to a set magnification in two dimensions over the sample 60 by scan coils 59 that are controlled by electrical currents supplied from a scan coil control power supply 74. Secondary signals 62 such as secondary electrons produced from the sample 60 by irradiation by the primary electron beam travel to over the objective lens 57 and then are detected by a secondary signal detector 63. The signals detected by the secondary signal detector 63 are amplified by a signal amplifier 64 and then transferred to an image memory 75 and displayed as a sample image on an image display device 76. A program for analyzing image information transferred to the image memory 75 and evaluating the brightness is loaded in the CPU 90. The CPU 90 can also function as an image analyzer.

One stage of deflection coil 101 is disposed near or in the same position as the scan coils 59 and operates as an aligner for the objective lens. The operation of the deflection coil 101 is controlled by an electrical current supplied from an aligner control power supply 81 for the objective lens. An octopole astigmatism-correcting coil 102 for correcting the astigmatism in the X- and Y-directions is disposed between the objective lens and the apertured plate. The astigmatism-correcting coil 102 is controlled by an electrical current supplied from an astigmatic corrector control power supply 82 to control the astigmatism in the primary electron beam 54. An aligner 103 for correcting axial deviation of the astigmatism-correcting coil is disposed near or in the same position as the astigmatism-correcting coil. The operation of the aligner 103 is controlled by an electrical current supplied from an aligner control power supply 83 for the astigmatic corrector.

Various manipulation buttons for making settings on the electron optical system and on scanning conditions can be displayed on the image display device 76, as well as images of the sample. In addition, a button for checking axial conditions and a button for giving an instruction for starting automated axial alignment can be displayed.

When the primary electron beam 54 has passed through a position located off the center of the objective lens 57 (i.e., in a state in which axial deviation has occurred), if the focus is adjusted, the field of view is moved concomitantly with the focus adjustment. If the operator notices the axial deviation, he/she can give an instruction for starting processing for axial alignment by manipulating (e.g., clicking on it with the mouse) a processing start button displayed on the display device. When the instruction for the axial alignment is received from the operator, the control CPU 90 starts the processing along the flow illustrated in FIG. 10.

Embodiment 2

Figure 10:
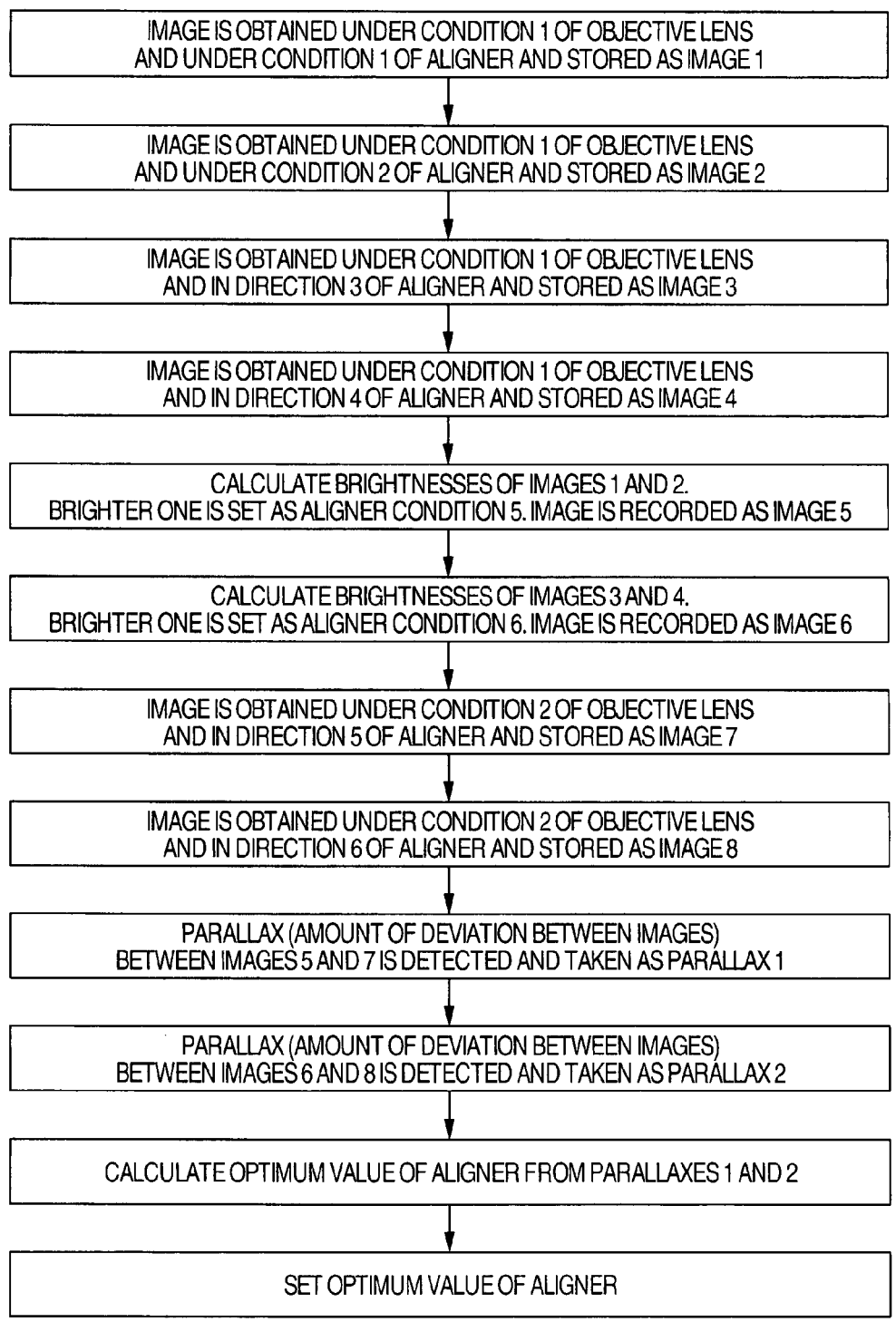
FIG. 10 is a schematic flow of processing for correcting axial deviation relative to an objective lens.

The flow of processing of FIG. 10 is described in detail in the following.

In step 1, the present condition of the objective lens 57 or a condition determined based on the present condition (e.g., a condition slightly shifted in terms of focus from the present focal condition) is set as condition 1 into the objective lens 57. Then, the present condition of the aligner 101 or a previously determined condition is set as condition 1 for the aligner 101. Image 1 is obtained under these objective lens condition 1 and aligner condition 1.

Figure 11:
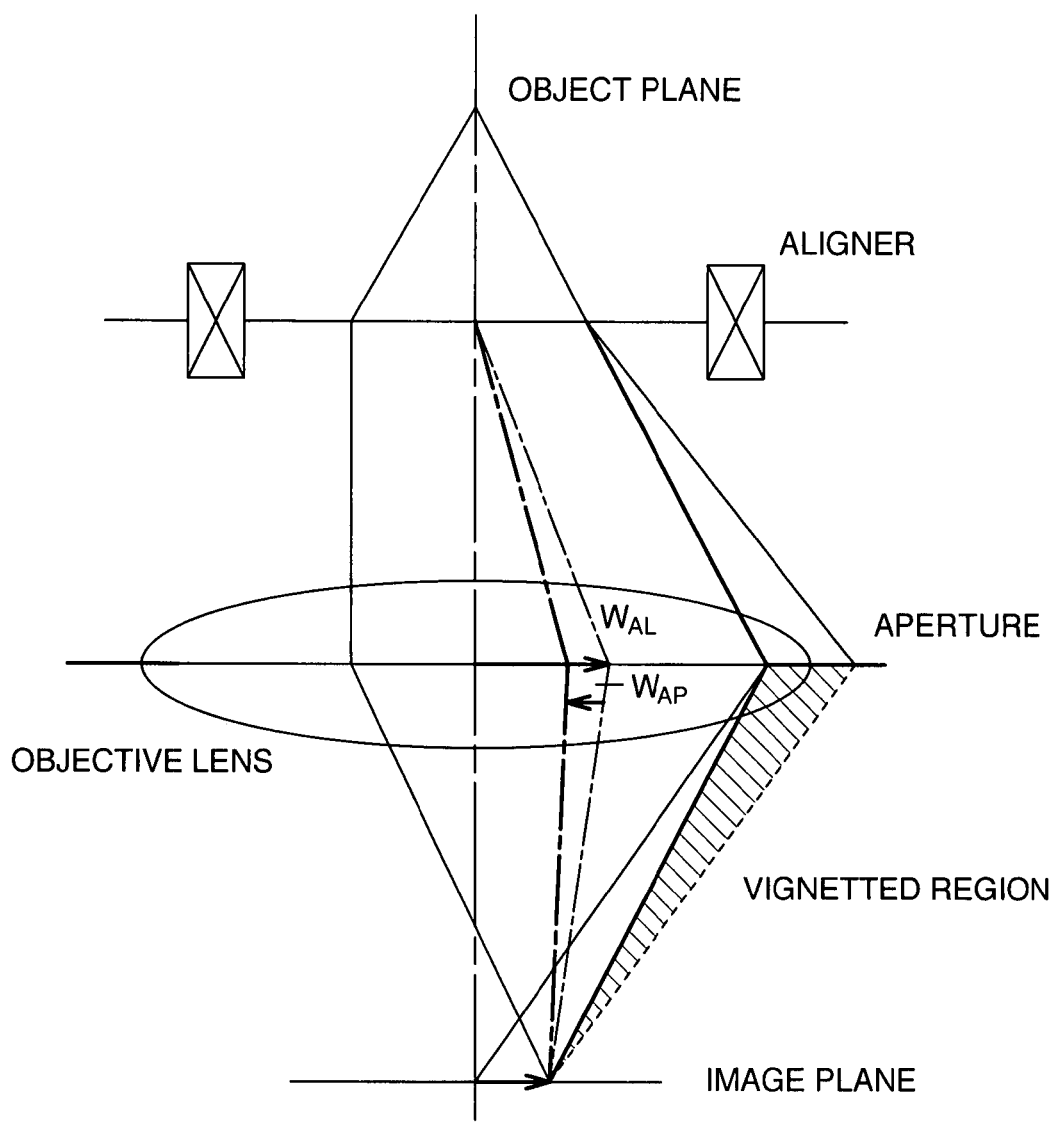
FIG. 11 is an explanatory diagram of the deflection direction of the aligner.

In step 2, condition 2 of the aligner 101 is obtained as deflection condition for the aligner by deflecting condition 1 by 180° within a plane perpendicular to the optical axis as shown in FIG. 11. This condition 2 is set into the aligner 101. Image 2 is obtained under condition 1 of the objective lens 57.

In step 3, condition 3 is obtained as deflection condition for the aligner 101 by deflecting condition 1 or 2 of the aligner 101 by 90° within a plane perpendicular to the optical axis. This condition 3 is set into the aligner 101. Image 3 is obtained under condition 1 of the objective lens 57.

In step 4, condition 4 of the aligner 101 is obtained as deflection condition for the aligner by deflecting condition 3 by 180° within a plane perpendicular to the optical axis. This condition 4 is set into the aligner 101. Image 4 is obtained under condition 1 of the objective lens 57.

In step 5, the average brightnesses of images 1 and 2 are calculated using image analysis of the control CPU 90 and compared. An aligner condition in a brighter direction is registered as condition 5. The image is registered as image 5.

In step 6, the average brightnesses of images 3 and 4 are calculated using image analysis of the control CPU 90 and compared. An aligner condition in a brighter condition is registered as condition 6. The image is registered as image 6.

In step 7, the deflection condition for the aligner 101 is set as condition 5 into the aligner 101. A condition for the objective lens 57 is taken as condition 2. Image 7 is obtained.

In step 8, the deflection condition for the aligner 101 is set as condition 6 into the aligner 101. A condition for the objective lens 57 is taken as condition 2. Image 8 is obtained.

In step 9, an image is again obtained under the same condition as for the image 1 and registered as image 59.

In step 10, the parallax (deviation between images) between the images 5 and 7 is detected by image processing and registered as parallax 1. The parallax between images can be detected, for example, by finding the correlation between the images while shifting the images 5 and 7 pixel by pixel and finding an amount of deviation between the images that produces a maximum amount of correlation between the images. Besides, other image processing can be applied to the present embodiment if the processing is capable of detecting the parallax.

In step 11, the parallax between the images 6 and 8 is detected by image processing and registered as parallax 2.

In step 12, the parallax between the images 1 and 9 is detected by image processing and registered as parallax 3. Since the images 1 and 9 have been obtained under the same condition, if there is a deviation (parallax 3) between them, the deviation has been created by drift in the sample or beam.

In step 13, the drift component is detected from the parallax 3. The parallaxes 1 and 2 are compensated for drift components. That is, the drift components of the parallaxes 1 and 2 are removed. For example, if the images 1 and 9 are accepted at an interval of t seconds, the drift (d) per unit time (second) is given by d=(parallax 5)/t. On the other hand, if the images 1 and 2 are accepted at an interval of T12 and if the images 3 and 4 are accepted at an interval of T34, it follows that the parallaxes 1 and 2 contain drift components dxT12 and dxT34, respectively. Therefore, a precise parallax arising from an axial deviation can be calculated by subtracting the drift components from the parallaxes 1 and 2.

In step 14, an optimum value for the aligner 101 is calculated from the drift-compensated parallaxes 1 and 2 and set into the aligner. The optimum condition for the aligner is derived from the two parallaxes under the conditions described in patent reference 1.

In this way, according to the embodiment of the present invention, even where an aperture is present under the aligner, error due to the aperture is reduced. It is possible to cope with varying axial deviation conditions and operating conditions of the charged particle optical system (e.g., the beam energy, focal distance, and optical magnification). It is easy to accomplish automation of the axial adjustment.

The principle on which the accuracy of automated adjustment of axial deviation relative to the objective lens is improved by the flow of processing of FIG. 10 is described by referring to FIGS. 11 and 12. If the alignment condition is modified by the aligner, the center axis of the charged particle beam moves a distance given by WAL from the center of the objective lens over the objective lens.

However, in a scanning electron microscope having an apertured plate under the aligner, the apertured plate produces a vignetted region as indicated by the hatching in FIG. 12. That is, the charged particle beam does not reach the image plane. Because a less amount of charged particle beam reaches the sample than normal, the image is darker. The correlation value for detection of the parallax deteriorates, producing error in automatic adjustment.

Accordingly, as shown in FIG. 11, the number of directions of deflection of alignment is increased to four from two. The new 2 directions are obtained by converting the former two directions by 180°. The brightnesses of images are detected. The brightnesses in the 180° opposite deflection directions are compared. The direction of deflection in which a brighter image is produced is selected. Automated axial adjustment is made using the two directions of deflection in which the effect of vignetting is smaller. Consequently, even in a scanning electron microscope having an apertured plate under the aligner, automated axial adjustment can be performed with less error.

Embodiment 3

On the other hand, with respect to the astigmatic corrector 102, more accurate automated axial adjustment can be made by the flow of processing as illustrated in FIG. 10 in the present embodiment. The principle on which optimum conditions for astigmatic correction are derived from the obtained parallaxes is described in patent reference 2.

Embodiment 4

The flow of processing of FIG. 13 is described in detail in the following.

In step 1, the primary electron beam 53 is scanned over the aperture 61 using the aligner 101 to obtain an image of the aperture hole. The beam center axis is adjusted using the image of the aperture hole. An adjustment is made such that the primary electron beam 53 passes through the center of the aperture 61. The principle on which the optimum aligner conditions (i.e., under which the primary electron beam 53 passes through the center of the aperture 61) are derived from the obtained image of the aperture hole is based on a principle equivalent to the principle described in patent reference 1.

In step 2, the automated axial adjustment of embodiment 2 is executed to carry out an adjustment of the optical axis relative to the objective lens. According to this method, the primary electron beam 53 passes through the center of the aperture 56 before the automated axial adjustment is performed. In consequence, the effects of vignetting at the initial position of the beam can be reduced. Furthermore, if the amount of deflection of the aligner is appropriately set, automated axial adjustment can be made after determining the direction of deflection in advance without making a comparison between the directions of deflection as in embodiment 2. In this case, the number of necessary pixels is reduced and so the execution time can be shortened.

Embodiment 5

Since the aperture 56 is normally mounted coaxially with the objective lens 57, the optical axis can be roughly adjusted simply by adjusting the beam center axis relative to the aperture 56. Accordingly, where one wants to adjust the optical axis roughly, only the adjustment of the beam center axis relative to the aperture 56 as described in step 1 of embodiment 4 is carried out. Where one wants to perform adjustment accurately, both adjustment of the beam center axis and automated adjustment of the optical axis are carried out as in embodiment 4. In this way, the processing can be modified according to the required accuracy of adjustment.

Figure 14:
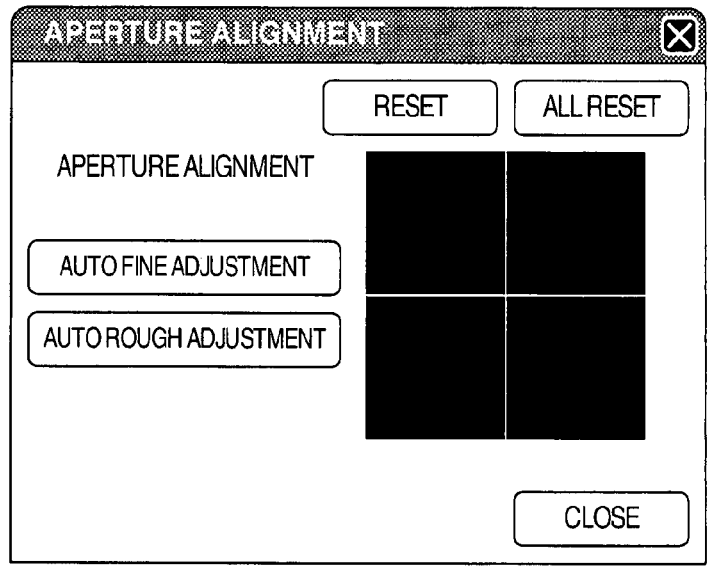
FIG. 14 is an image for manipulation of an automated function of adjusting the optical axis.
Figure 15:
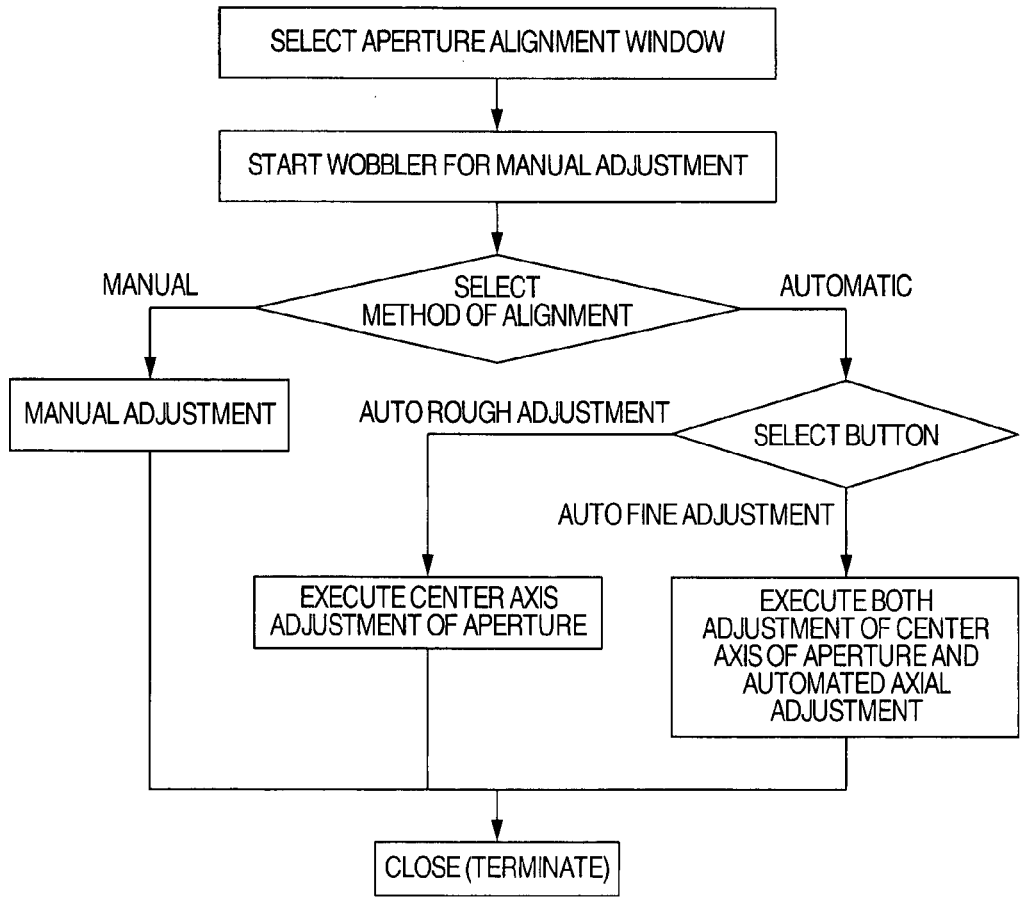
FIG. 15 is an image for manipulation of an automated function of adjusting the optical axis.

The above-described flow is described as embodiment 5 by referring to FIGS. 14 and 15. FIG. 14 is an image displayed on the image display device 76. When an adjustment of the optical axis is made, the user displays the image of FIG. 14 and performs a work for adjusting the axis along the flow illustrated in FIG. 15.

In this case, where the user wants to perform rough automated adjustment of the optical axis, the user depresses "auto rough adjustment". Where the user wants to perform accurate automated adjustment of the optical axis, the user depresses "auto fine adjustment". Symbols and characters marked on the buttons and the method of selecting an adjusted kind such as a button are not limited to such expressions.

Where the operator performs an adjustment of the optical axis, the operator first displays the image of FIG. 14 on the image display device 76. Simultaneously with display of the image, the excitation current of the objective lens begins to vary periodically for manual adjustment of the optical axis. Where the automated function of adjustment is not used, the operator manually adjusts the alignment deflector without depressing any button of FIG. 14. After end of the adjustment, the operator closes FIG. 14 and terminates the adjustment of the optical axis.

Where the automated function of adjustment is used, the operator depresses the button "auto rough adjustment" or the button "auto fine adjustment" in FIG. 14. Where "auto rough adjustment" is depressed, the control CPU 90 immediately performs an adjustment of the beam center axis relative to the aperture 61. In this case, the automated adjustment of the axis is not made. On the other hand, when the button "auto fine adjustment" is depressed, the control CPU 90 performs an adjustment of the beam center axis relative to the aperture 61 and an automated adjustment of the axis as in embodiment 4. After the end of the adjustment, the operator closes FIG. 14 and terminates the adjustment of the optical axis.

Where "auto rough adjustment" is performed, the adjustment of the beam center axis can be performed by acquiring a less number of images and so the processing can be carried out more quickly than the automated adjustment of the axis.

Automated axial adjustment has trouble in periodic samples. In adjustment of the center axis, what is scanned is the aperture and, therefore, the adjustment is not affected by the periodicity of the sample. Furthermore, in automated axial adjustment, the beam is scanned over the sample and so there is the anxiety that the sample is damaged by the charged particle beam during the scanning. In adjustment of the beam center axis, the beam is scanned over the aperture, thus eliminating the anxiety.

On the other hand, where "auto fine adjustment" is performed, the automated axial adjustment is made after performing an adjustment of the center axis. Therefore, it takes some time until the adjustment is completed. However, more accurate axial adjustment can be made than "auto rough adjustment", because mechanical error between the optical axis of the objective lens and the center axis of the aperture attached to the objective lens can be adjusted.

It should be further understood by those skilled in the art that although the foregoing description has been made on embodiments of this invention, the invention is not limited thereto and various changes and modifications may be made without departing from the spirit of the invention and the scope of the appended claims.

The invention claimed is:

1. An observation apparatus using scanning electron microscope comprising:
   (i) a source of electrons;
   (ii) converging lenses for converging a primary electron beam emitted from the source of electrons;
   (iii) an objective lens for focusing the primary electron beam onto a sample;
   (iv) a detector for detecting a secondary signal in response to the irradiation by the primary electron beam; and
   (v) a scanning deflector disposed between the converging lenses and the objective lens, the scanning electron microscope comprising:
   an objective aperture disposed between the scanning deflector and the converging lenses in order to limit an irradiation amount of the primary electron beam onto the sample;
   an aligner for deflecting a center of the primary electron beam on the objective aperture, and
   a computer for obtaining optical axis correction amount of the primary electron beam by the aligner,
   wherein the computer utilizes a first image of the objective aperture obtained by not operating the aligner, a second image obtained by deflecting the primary electron beam a predetermined amount by said aligner in the X-direction without displacement in the Y-direction on said objective aperture, and a third image obtained by deflecting the primary electron beam a predetermined amount by the aligner in the Y-direction without displacement in the X-direction on the objective aperture so as to compensate an optical axis of the primary electron beam by way of obtaining an alignment condition of the electron beam and objective aperture that shows no movement of the center of the image depending on a relative sensitivity in the X- and Y-directions of the aligner.

2. The observation apparatus according to claim 1, wherein:
   the computer further: detects center positions of the objective aperture in each of the first image, the second image and the third image, respectively,
   calculates sensitivity of the aligner by applying the information of the center positions into formula determining the difference in image deviation of the second and third images as compared to the first image when the aligner aligns the particle beam in the x and y-directions, respectively, and
   controls a condition of the aligner under the condition where the center of image displaying image screen for adjustment and the center of image screen for adjustment such that the first image is moved a given amount toward the center.

3. The observation apparatus according to claim 1, wherein:
   the computer carries out another deflection control by the scanning deflector for minimizing the scanning width of the primary electron beam on the sample is carried out when obtaining the first image, the second image, and the third image, in addition to deflection by the aligner.

4. The observation apparatus according to claim 1, wherein:
   the computer carries out a control of changing brightness and contrast in a case of obtaining the first image, the second image, and the third image.

5. The observation apparatus according to claim 1, wherein:
   the computer sets a scanning line width of the aligner on the objective aperture in accordance with a crossover position of the primary electron by the converging lenses.

* * * * *